(12) United States Patent
Theodoridis et al.

(10) Patent No.: US 6,277,847 B1
(45) Date of Patent: Aug. 21, 2001

(54) HERBICIDAL ISOINDOLINONYL-AND 3,4-DIHYDROISOQUINOLONYL-SUBSTITUTED HETEROCYCLES

(75) Inventors: George Theodoridis, Princeton; Scott D. Crawford, Jackson, both of NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/538,800

(22) Filed: Mar. 30, 2000

Related U.S. Application Data

(60) Provisional application No. 60/127,700, filed on Apr. 2, 1999.

(51) Int. Cl.$^7$ .................. C07D 219/00; C07D 401/04; C07D 209/44; A61K 31/47; A61K 31/505
(52) U.S. Cl. .......... 514/241; 546/141; 546/120; 514/309; 514/274; 514/414; 514/254; 514/303; 514/406; 514/266; 514/403; 514/392; 514/384; 514/242; 544/310; 544/236; 544/223; 544/235; 544/282; 544/182; 548/455; 548/364.7; 548/360.1; 548/312.1; 548/263.2
(58) Field of Search ................... 546/141, 120; 514/309, 274, 414, 254, 303, 241, 406, 266, 403, 392, 384, 242; 544/310, 236, 223, 235, 282, 182; 548/455, 364.7, 360.1, 312.1, 263.2

Primary Examiner—Richard L. Raymond
Assistant Examiner—Hong Liu
(74) Attorney, Agent, or Firm—FMC Corporation

(57) ABSTRACT

This invention relates to herbicidal compounds of formula (I), methods of making such herbicidal compounds and methods of using such herbicidal compounds. It has been found that compounds of formula (I) are useful as pre-emergent and post-emergent herbicides. Formula (I) is as follows:

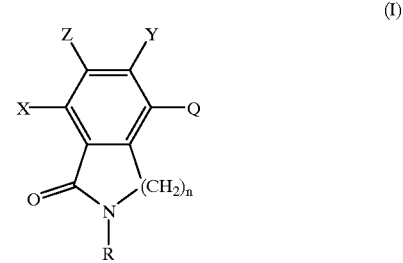

where Q, X, Y, n, and R are as described herein. This invention is also directed to intermediates used in the preparation of such herbicidal compounds.

10 Claims, No Drawings

HERBICIDAL ISOINDOLINONYL-AND 3,4-DIHYDROISOQUINOLONYL-SUBSTITUTED HETEROCYCLES

This is a nonprovisional of Application No. 60/127,700, files Apr. 2, 1999.

FIELD OF THE INVENTION

This invention relates to herbicidal compounds of formula (I), methods of making such herbicidal compounds and methods of using such herbicidal compounds. This invention also relates to intermediates used in the preparation of such herbicidal compounds.

BACKGROUND OF THE INVENTION

There is a continuing demand for new herbicides. Herbicides are useful for controlling unwanted vegetation, i.e., weeds, which may otherwise cause significant damage to crops such as wheat, corn, soybeans and cotton, to name a few. For crop protection, so-called "selective" herbicides are desired that control the weeds without damaging the crop to any significant degree. Such crops are said to exhibit tolerance to the herbicide. In certain other situations, it is desirable to use herbicides that provide complete vegetation control such as in areas around railroad tracks and other structures. While many commercial products are available that provide selective or complete vegetation control, demand exists for new herbicides that are more effective and less costly, and meet requisite safety characteristics. Additionally, as an aid to harvesting there is also a demand for new, safe, more effective, and less costly compounds that cause defoliation and/or desiccation of cultivated plant parts. Such compounds would be useful in the harvesting of, for example, cotton, potatoes, rape, sunflowers, soybeans and broadbeans.

OBJECTS AND SUMMARY OF THE INVENTION

It has now been found that certain novel isoindolinonyl- and 3,4-dihydroisoquinolonyl-substituted heterocycles are useful as pre-emergent and post-emergent herbicides. These herbicidally effective compounds are represented by formula (I):

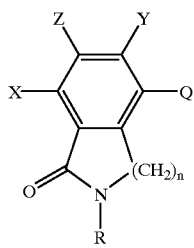

wherein Q is:

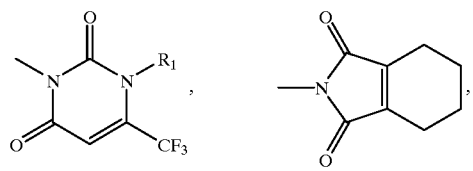

-continued

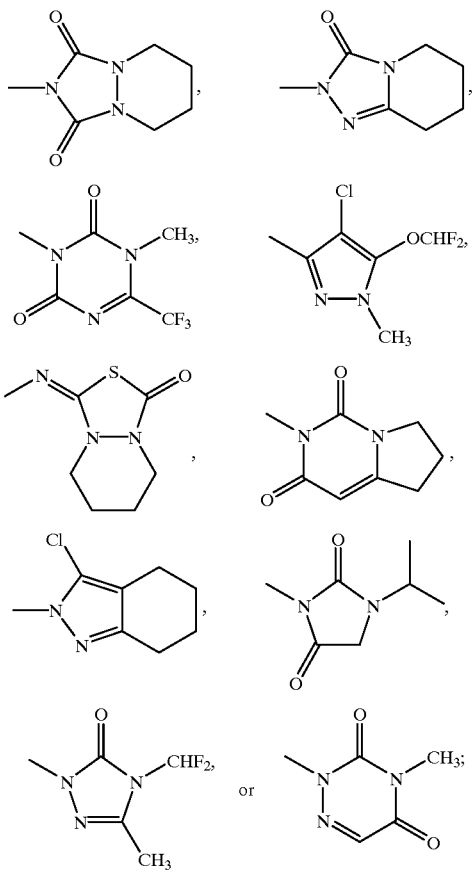

X, Y and Z are as follows: (i) X is hydrogen, halogen, alkyl, haloalkyl, alkoxyl, haloalkoxyl, cyano, amido or nitro; Y is hydrogen, halogen, alkyl, or haloalkyl; and Z is hydrogen, alkyl, halogen, amino, nitro, alkoxyl, hydroxyl or haloalkoxyl with the proviso that when Z is alkyl, halogen, amino, nitro, alkoxyl, hydroxyl or haloalkoxyl, X is not a hydrogen and Y is not a hydrogen; or (ii) X and Z are connected to each other to form part of a 4, 5 or 6 membered ring and Y is as defined above, or Y and Z are connected to each other to form part of a 4, 5 or 6 membered ring and X is as defined above;

n is 1 or 2;

R is hydrogen, amino, alkyl, haloalkyl, cyanoalkyl, hydroxyl, alkoxyl, alkoxyalkyl, cycloalkylalkyl, alkenyl, alkenoxy, alkynyl, alkoxycarbonylalkyl, or phenylalkyl; and $R_1$ is hydrogen, amino, alkyl, haloalkyl, alkoxyalkyl, cyanoalkyl, arylalkyl, alkenyl, alkynyl, alkoxycarbonylalkyl, or salts thereof.

The present invention is also directed to compounds of formulas (II) and (III), which are used as intermediates in the preparation of formula (I). Formula (II) is as follows:

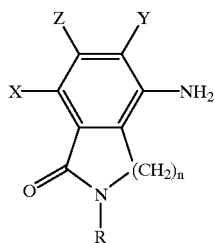

(II)

wherein:

X, Y and Z are as follows: (i) X is hydrogen, halogen, alkyl, haloalkyl, alkoxyl, haloalkoxyl, cyano, amido or nitro; Y is hydrogen, halogen, alkyl, or haloalkyl; and Z is hydrogen, alkyl, halogen, amino, nitro, alkoxyl, hydroxyl or haloalkoxyl with the proviso that when Z is alkyl, halogen, amino, nitro, alkoxyl, hydroxyl or haloalkoxyl, X is not a hydrogen and Y is not a hydrogen; or (ii) X and Z are connected to each other to form part of a 4, 5 or 6 membered ring and Y is as defined above, or Y and Z are connected to each other to form part of a 4, 5 or 6 membered ring and X is as defined above;

n is 1 or 2, and;

R is hydrogen, amino, alkyl, haloalkyl, cyanoalkyl, hydroxyl, alkoxyl, alkoxyalkyl, cycloalkylalkyl, alkenyl, alkenoxyl, alkynyl, alkoxycarbonylalkyl, or phenylalkyl.

Formula (III) is as follows:

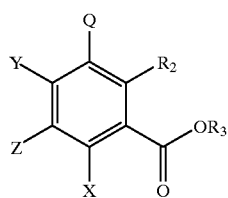

(III)

wherein Q is:

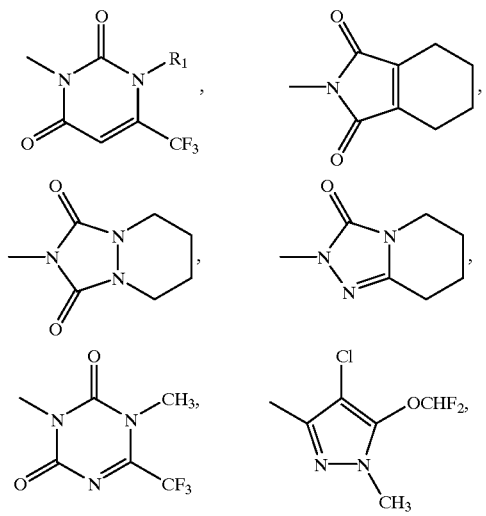

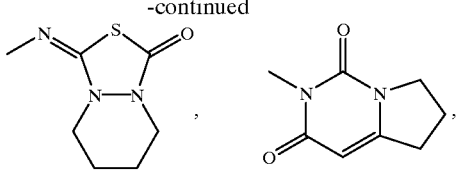

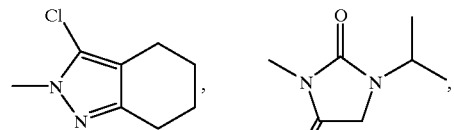

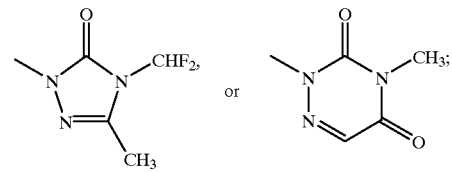

X, Y and Z are as follows: (i) X is hydrogen, halogen, alkyl, haloalkyl, alkoxyl, haloalkoxyl, cyano, amido or nitro; Y is hydrogen, halogen, alkyl, or haloalkyl; and Z is hydrogen, alkyl, halogen, amino, nitro, alkoxyl, hydroxyl or haloalkoxyl with the proviso that when Z is alkyl, halogen, amino, nitro, alkoxyl, hydroxyl or haloalkoxyl, X is not a hydrogen and Y is not a hydrogen; or (ii) X and Z are connected to each other to form part of a 4, 5 or 6 membered ring and Y is as defined above, or Y and Z are connected to each other to form part of a 4, 5 or 6 membered ring and X is as defined above;

$R_1$ is hydrogen, amino, alkyl, haloalkyl, alkoxyalkyl, cyanoalkyl, arylalkyl, alkenyl, alkynyl, alkoxycarbonylalkyl, or salts thereof;

$R_2$ is methyl or halomethyl, and;

$R_3$ is alkyl.

The present invention is further directed to methods of using and making compounds of formula (I), herbicidal compositions comprising at least one compound of formula (I) and pesticidal compositions comprising at least one compound of formula (I).

DETAILED DESCRIPTION OF THE INVENTION

The present invention relates to certain new and useful agricultural compounds, namely, certain novel isoindolinonyl- and 3,4-dihydroisoquinolonyl-substituted heterocycles, that possess pre-emergent and post-emergent herbicidal activity. These compounds are represented by formula (I) as defined hereinabove.

The alkyl group which may represent X in formula (I) may be a substituted or unsubstituted, branched or straight chain, alkyl group containing $C_1$–$C_{10}$ carbon atoms, preferably, $C_1$–$C_6$ carbon atoms. The alkyl portion of the haloalkyl group, alkoxyl group and haloalkoxyl group which may represent X in formula (I) may be a substituted or unsubstituted, branched or straight chain, alkyl group containing $C_1$–$C_6$ carbon atoms, preferably, $C_1$–$C_3$ carbon atoms. The halogen atom which may represent X in formula (I) may be a chlorine atom, fluorine atom, bromine atom or iodine atom, preferably, a chlorine atom.

The alkyl group, as well as the alkyl portion of the haloalkyl group, which may represent Y in formula (I) may be a substituted or unsubstituted, branched or straight chain, alkyl group containing $C_1$–$C_6$ carbon atoms, preferably, $C_1$–$C_3$ carbon atoms. The halogen which may represent Y in formula (I) may be a chlorine atom, bromine atom or fluorine atom, preferably, a chlorine atom.

The alkyl group, as well as the alkyl portion of the haloalkyl group, which may represent R in formula (I) may be a substituted or unsubstituted, branched or straight chain, alkyl group containing $C_1$–$C_{10}$ carbon atoms, preferably $C_1$–$C_6$. The alkyl portion of the alkoxyl group which may represent R in formula (I) may be a substituted or unsubstituted, branched or straight chain, alkyl group containing $C_1$–$C_6$ carbon atoms, preferably, $C_1$–$C_3$ carbon atoms. The phenylalkyl group representing R in formula (I) may be substituted with, for example, one or more of a halogen atom or alkoxyl group.

The alkyl group which may represent $R_1$ in formula (I) may be a substituted or unsubstituted, branched or straight chain, alkyl group containing $C_1$–$C_6$ carbon atoms, preferably, $C_1$–$C_3$ carbon atoms.

The structural moieties representing Q in formula (I) may also be identified by their chemical names as follows:

Q1
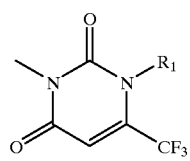

Q2
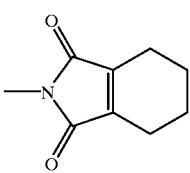

Q3
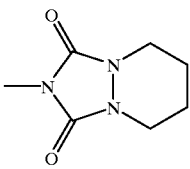

Q4
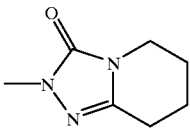

Q5
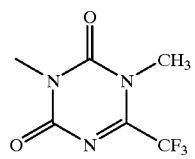

Q6
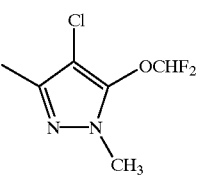

Q7
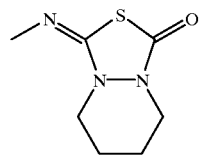

Q8
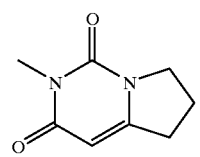

Q9
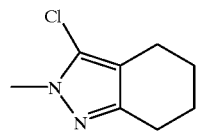

Q10
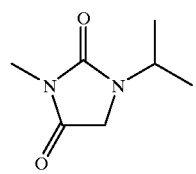

Q11
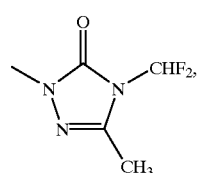

Q12
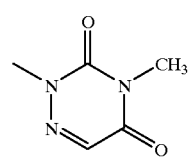

where "Q1" is 1-substituted-6-trifluoromethyl-2,4(1H,3H)-pyrimidinedion-3-yl; "Q2" is 3,4,5,6-tetrahydrophthalimid-1-yl; "Q3" is 1,6,8-triazabicyclo[4.3.0]nonane-7,9-dion-8-yl; "Q4" is 5,6,7,8-tetrahydro-1,2,4-triazolo[4,3-A]pyridin-3(2H)-on-2-yl; "Q5" is 1-methyl-6-trifluoromethyl-1,3,5-triazine-2,4-dione-3-yl; "Q6" is 4-chloro-5-difluoromethoxy-1-methylpyrazol-3-yl; "Q7" is 5,6,7,8-tetrahydro-1H,3H[1,3,4]thiadiazolo[3,4-a]pyridazineimin-1-yl; "Q8" is 1,2,3,6-tetrahydro-6-azaindolizin-5,7-dion-6-yl; "Q9" is 3-chloro-4,5,6,7-tetrahydroindazol-3-yl; "Q10" is 1-(1-methylethyl)imidazolidine-2,4-dion-3-yl; "Q11" is 4-difluoromethyl-4,5-dihydro-3-methyl-1,2,4-triazol-5(1H)-on-1-yl; and "Q12" is 4-methyl-1,2,4-triazine-3,5-dion-2-yl.

Where X and Z or Y and Z are connected to form part of a 4, 5 or 6 membered ring, X and Z or Y and Z, taken together, may be: —$C_3H_6$—, —$C_4H_8$—, —$CH_2CH_2O$—, —$CH_2CH_2C(CH_3)_2O$—, —$OCH_2O$—, —$OCH_2CH_2O$—, —$OCF_2CF_2$—, —$CF_2CF_2O$—, —$OCF_2O$—, —$OCF_2CF_2O$—, CH═CHCH═CH—, —CH═CHO—, —CH═CHN—, —CH═C(Br)N—, —CH═C(CF_3)N—, —CH═C(CN)N—, —CH═C(NO_2)N—, —CH═CHS—, —CH═NCH═CH—, —CH═C(CH_2OCH_3)O—, —CH=C(CH₃)S—, —CH=NN(CH₃)—, —CH=NN(C₂H₅)—, —C(CH₃)=NN(CH₃)—, —CH=CHCH=N—, —N=CHNH—, —C(Cl)=CHCH=CH—, —CH=C(Br)CH=CH—, —CH=C(CH₃)CH=CH—, —C(CF₃)=CHCH=CH—, —CH=CHC(Cl)=CH—, —CH=C(NO₂)CH=N—, —OCH=CH—, —OCH=N—, —CH=C(CF₃)CH=N—, —CH=CHCH=C(Cl)—, C(CF₃)=CHCH=CH—, —SCH=CH—, —C(Cl)=NCH=CH—, —CH₂SCH₂—, —CH₂S(O)CH₂—, —CH₂S(O)₂CH₂—, —SN=N—, —CH₂N(C₂H₅)CH₂—, —N(CH₃)CH=CH—, —N(CH₂Ph)CH=CH—, —N=CHS—, —N=CHO—, —N=C(CH₃)S—, —N=CHCH=CH—, —NHCH=N—, —CH=CHN=CN—, —CH=NCH=CH—, —CH=CHC(NO₂)=CH—, —CH=CHCH=N— or —N=CHC(CF₃)=CH—.

The halogens which may represent Z include chloro, fluoro and bromo, preferably, chloro and fluoro, more preferably, fluoro. The alkyl group and alkyl portion of the alkoxyl group which may represent Z may be a substituted or unsubstituted, branched or straight chain, alkly group containing C₁–C₃ carbon atoms, preferably, C₁. Examples of the halomethyl group which may represent Z include CH₂Br and CH₂Cl, preferably, CH₂Br.

One aspect of this invention relates to compounds of formula (I) where Q is 1-substituted-6-trifluoromethyl-2,4 (1H,3H)-pyrimidinedion-3-yl and X, Y, Z, n, R and R₁ are as described above.

Another aspect of this invention relates to compounds of formula (I) where Q is 3,4,5,6-tetrahydrophthalimid-1-yl and X, Y, Z, n, R and R₁ are as described above.

Another aspect of this invention relates to compounds of formula (I) where Q is 1,6,8-triazabicyclo[4.3.0]nonane-7,9-dion-8-yl and X, Y, Z, n, R and R₁ are as described above.

Another aspect of this invention relates to compounds of formula (I) where Q is 5,6,7,8-tetrahydro-1,2,4-triazolo[4,3-A]pyridin-3(2H)-on-2-yl and X, Y, Z, n, R and R₁ are as described above.

Another aspect of this invention relates to compounds of formula (I) where Q is 1-methyl-6-trifluoromethyl-1,3,5-triazine-2,4-dione-3-yl and X, Y, Z, n, R and R₁ are as described above.

Another aspect of this invention relates to compounds of formula (I) where Q is 4-chloro-5-difluoromethoxy-1-methylpyrazol-3-yl and X, Y, Z, n, R and R₁ are as described above.

Another aspect of this invention relates to compounds of formula (I) where Q is 5,6,7,8-tetrahydro-1H,3H[1,3,4]thiadiazolo[3,4-a]pyridazineimin-1-yl and X, Y, Z, n, R and R₁ are as described above.

Another aspect of this invention relates to compounds of formula (I) where Q is 1,2,3,6-tetrahydro-6-azaindolizin-5,7-dion-6-yl and X, Y, Z, n, R and R₁ are as described above.

Another aspect of this invention relates to compounds of formula (I) where Q is 3-chloro-4,5,6,7-tetrahydroindazol-3-yl and X, Y, Z, n, R and R₁ are as described above.

Another aspect of this invention relates to compounds of formula (I) where Q is 1-(1-methylethyl)imidazolidine-2,4-dion-3-yl and X, Y, Z, n, R and R₁ are as described above.

Another aspect of this invention relates to compounds of formula (I) where Q is 4-difluoromethyl4,5-dihydro-3-methyl-1,2,4-triazol-5(1H)-on-1-1yl and X, Y, Z, n, R and R₁ are as described above.

Another aspect of this invention relates to compounds of formula (I) where Q is 4-methyl-1,2,4-triazine-3,5-dion-2-yl and X, Y, Z, n, R and R₁ are as described above.

Preferred compounds of formula (I) include the following: X is chloro; Y is hydrogen or fluoro; and R is alkyl, cycloalkylalkyl, haloalkyl, alkynyl or alkoxyalkyl.

Particularly preferred compounds of formula (I) include the following: Q is 1-substituted-6-trifluoromethyl-2,4(1H,3H)-pyrimidinedion-3-yl; X is chloro; Y is hydrogen or fluoro; n is 1; R is 1-methylethyl; and R₁ is methyl or amino.

The present invention is also directed to compounds represented by formula (II) and (III), which are intermediates used in preparing compounds of formula (I). Formula (II) is as follows:

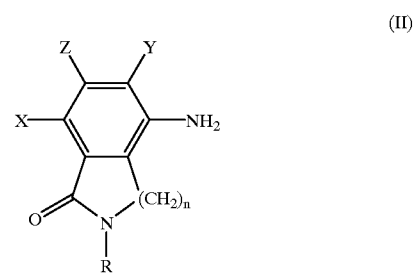

(II)

wherein X, Y, n, Z and R are as defined hereinabove with respect to formula (I).

Preferred X, Y, Z, n and R in formula (I) include those set forth hereinabove for formula (I). For example, preferred compounds of formula (I) include the following: X is chloro; Y is hydrogen or fluoro; n is 1; and R is alkyl, cycloalkylalkyl, haloalkyl, alkynyl, or alkoxyalkyl. Also, the phenylalkyl group representing R in formula (II) may be substituted with, for example, one or more of a halogen or alkoxyl group.

Formula (III) is as follows:

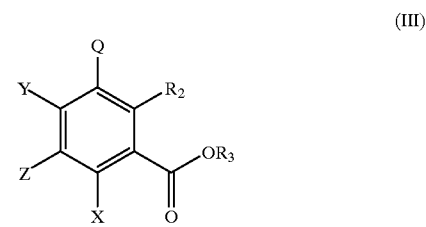

(III)

wherein Q, X, Y, Z and R₁ in formula (III) are as defined hereinabove with respect to formula (I); R₂ is a methyl or halomethyl group; and R₃ is an alkyl group.

Preferred Q, X, Y, Z and R₁ in formula (III) include those set forth hereinabove for formula (I). Particularly preferred compounds of formula (III) include the following: Q is 1-substituted-6-trifluoromethyl-2,4(1H,3H)-pyrimidinedion-3-yl (Q1); X is chloro; Y is hydrogen or fluoro; and R₁ is hydrogen, methyl, or amino.

As used in this specification and unless otherwise indicated, the alkyl group or alkyl portion of any substituent representing X, Y, R₁, R₂, R₃ and Z may be a substituted or unsubstituted, straight or branched chain. Also, unless indicated otherwise, X, Y, Z, n, R and R₁ are the same for formulas (II) and (III) as they are for formula (I).

The term "uracil moiety" and the term "1-substituted-6-trifluoromethyl-2,4(1H,3H)-pyrimidinedion-3-yl" are one and the same, and both terms are employed interchangeably hereinafter. The term "uracil" refers to those intermediates or compounds of formula (I) of the present invention containing the uracil moiety.

Schemes 1 and 2 below illustrate procedures for synthesizing compounds of formula (I) from methyl 2-methyl-3-nitrobenzoate A using formula (II) and (III).

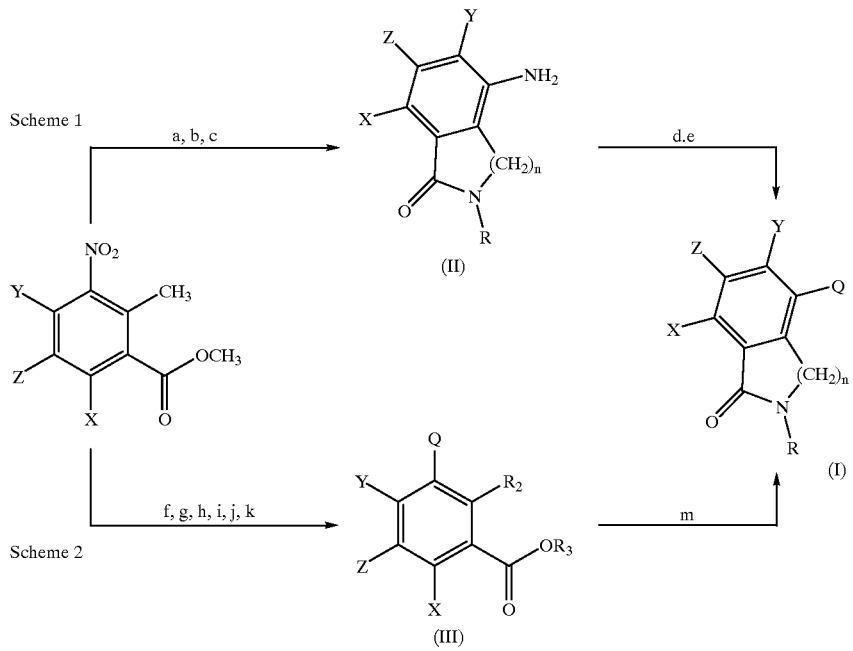

Scheme 1

Scheme 2

(a) NBS/uv/CCl$_4$, RNH$_2$/Et$_2$O, (b) Fe/HOAc/H$_2$O/50° C. (c) NCS/DMF, (d) ClCO$_2$CCl$_3$/Toluene/reflux, (CF$_3$)(NH$_2$)C=CCO$_2$C$_2$H$_5$/NaH/THF, (e) R$_1$I/K$_2$CO$_3$/DMF, (f) H$_2$/5% Pd on C/EtOH, (g) NCS/DMF, (h) ClCO$_2$CCl$_3$/Toluene/reflux, (i) (CF$_3$)(N H$_2$)C=CCO$_2$C$_2$H$_5$/NaH/THF, (j) R$_1$I/K$_2$CO$_3$/DMF, (k) NBS/(C$_6$H$_5$CO)$_2$O$_2$/CCl$_4$, (m) RNH$_2$THF. R and R$_1$ are generally as defined herein with respect to formula (I).

According to Scheme 1, compounds of the present formula (I), for example, where Q is a uracil moiety (Q1) and n is 1, may be synthesized in a step-wise manner by first forming the isoindolin-1-one ring, then preparing the attached uracil moiety. For example, according to step (a), chlorination of intermediate A with NBS under ultraviolet light in an appropriate aprotic solvent (selected from, but not limited to, heptane, dioxane, toluene, diethyl ether, carbon tetrachloride, chloroform, methylene chloride, acetone, acetonitrile, EtOAc, DMF, or dimethyl sulfoxide;) affords the corresponding alkyl 2-bromomethyl-3-nitrobenzoate. Without isolation, cyclization of the 2-bromomethyl intermediate with an appropriate alkylamine, such as 1-methylethylamine, yields the corresponding 2-alkyl-4-nitroisoindolin-1-one, which when subjected to reduction with iron powder in HOAc/water, according to step (b), gives the corresponding 2-alkyl-4-aminoisoindolin-1-one (a compound of formula (II)). The optional halogenation of the 2-alkyl-4-aminoisoindolin-1-one with, for example, NCS in an appropriate aprotic solvent according to step (c), affords additional examples of the 2-alkyl-4-aminoisoindolin-1-one where X (in formula (II)), or X and Y, are halogen such as chlorine. According to step (d), reaction of the 2-alkyl-4-aminoisoindolin-1-one 1 with trichloromethyl chloroformate in an aprotic solvent yields the isocyanate of the 2-alkyl-4-aminoisoindolin-1-one, which upon reaction with ethyl 3-amino-4,4,4-trifluoro-2-butenoate under mildly basic conditions conferred by, for example, sodium hydride or the like, in an aprotic solvent gives the corresponding isoindolinonyl-derived 1-unsubstituted uracil. Alkylation of the isoindolinonyl-derived 1-unsubstituted uracil, according to step (e), with an alkyl halide, such as methyl iodide, under basic conditions conferred by, for example, potassium carbonate or the like, in an aprotic solvent, affords a compound of formula (I), where Q is a uracil moiety (Q1).

According to Scheme 2, in an alternate method, compounds of formula (I), for example, where Q is a uracil moiety (Q1) and n is 1, may be synthesized in a step-wise manner by first forming the uracil moiety, then preparing the attached isoindolinonyl ring. For example, according to step (f), reduction of intermediate A in the presence of 5% palladium on carbon in a protic solvent (selected from, but not limited to, diethylamine, HOAc, trifluoroacetic acid, methanol, ethanol, ammonia, ethylene glycol, formic acid or water), preferably, ethanol, affords the corresponding alkyl 2-alkyl-3-aminobenzoate. In a manner analogous to step (c) above, the optional halogenation of the 3-aminobenzoate with NCS, according to step (g), affords additional alkyl 2-alkyl-3-aminobenzoate intermediates where X, or X and Y, are halogen such as chlorine. According to step (h), and in a manner analogous to the first part of step (d) above, reaction of the 2-alkyl-3 -aminobenzoate with trichloromethyl chloroformate yields the corresponding isocyanate. The reaction of the so-prepared isocyanate with 3-amino-4, 4,4-trifluoro-2-butenoate according to step (i) in a manner analogous to the second part of step (d) above, in turn gives the corresponding alkyl 6-optionally-substituted-2-alkyl-3-(1-unsubstituted uracil-derived)benzoate. According to step (j), alkylation of the so-prepared alkyl 2-alkyl-3-(1-unsubstituted uracil-derived)benzoate with an alkyl halide in a manner analogous to step (e) above, provides the corresponding alkyl 2-alkyl-3-(1-substituted uracil-derived) benzoate (a compound of formula (III)). Treatment of the alkyl 2-alkyl-3-(1-substituted uracil-derived)benzoate, where R$_2$ is methyl, according to step (k), with NBS in the presence of, for example, benzoyl peroxide, in an aprotic solvent such as carbon tetrachloride, yields the corresponding alkyl 2-bromoalkyl-3-(1-substituted uracil -derived) benzoate (a compound of formula (III)), where R$_2$ is bromomethyl. Cyclization, where R$_2$ is bromomethyl, according to step (m), with an appropriate amine, such as 1,1-dimethylethylamine, in an aprotic solvent, such as THF, yields the compounds of formula (I) where Q is a uracil moiety (Q1).

Other compounds of the present formula (I) may be prepared using compounds of formula (II). For example, cyclization of a compound of formula (II) with 3,4,5,6-tetrahydrophthalic anhydride in a protic solvent, such as HOAc, yields (I), the compounds of the present invention where Q is 3,4,5,6-tetrahydrophthalimid-1-yl (Q2). In a related manner, compounds of formula (II) may be converted to the corresponding hydrazine hydrochloride under Sandmeyer conditions which, when treated with O-methylvalerolactin in the presence of a strong acid, such as concentrated sulfuric acid, in protic solvents, such as HOAc and methanol, yields the corresponding (aza-2-piperidylidenemethyl)(2-substituted-isoindolin-1-on-4-yl) amine. Treatment of the so-prepared amine with n-butyllithium and cyclization with ethyl chloroformate in an aprotic solvent such as THF, affords a compound of formula (I) where Q is 5,6,7,8-tetrahydro-1,2,4-triazolo[4,3-A]pyridin-3(2H)-on-2-yl (Q4).

The compounds of formula (I), (II) and (III) wherein X and Z or Y and Z are connected to each other to form part of a 4, 5 or 6 membered ring can be prepared in a similar manner as disclosed above in Scheme 1 and 2 from the corresponding intermediate A.

The present invention also relates to herbicidal compositions that combine herbicidally effective amounts of at least one compound of formula (I) with adjuvants and carriers normally employed in the art. The present herbicidal compounds may be formulated for agricultural use as granules having relatively large particle size (for example, 8/16 or 4/8 US Mesh), as water-soluble or water-dispersible granules, as powdery dusts, as wettable powders, as emulsifiable concentrates, as solutions, or as any of other known types of agriculturally-useful formulations, depending on the desired mode of application.

These herbicidal compositions may be applied either as water-diluted sprays, dusts, granules or wettable powders to the areas in which suppression of vegetation is desired. These herbicidal compositions may contain as little as about 0.1%, 0.2% or 0.5% to as much as about 95% or more by weight of a compound of formula (I) to inactive ingredient. Also, more than one compound of formula (I) may be present in the composition together with one or more other pesticides.

Dusts are free flowing admixtures of the compounds of formula (I) with finely divided solids such as talc, natural clays, kieselguhr, flours such as walnut shell and cottonseed flours, and other organic and inorganic solids which act as dispersants and carriers for the toxicant. These finely divided solids generally have an average particle size of less than about 50 microns. A dust formulation useful herein is one containing about 1.0 part or less of the compound of formula (I) and 99.0 parts of talc.

Wettable powders are in the form of finely divided particles which disperse readily in water or other dispersant. The wettable powder may ultimately be applied to the soil as a dry dust or as an emulsion in water or other liquid. Typical carriers for wettable powders include Fuller's earth, kaolin clays, silicas, and other highly absorbent, readily wet inorganic diluents. The wettable powders may generally contain about 5–80% of a compound of formula (I), depending on the absorbency of the carrier, and usually also contain a small amount of a wetting, dispersing or emulsifying agent to facilitate dispersion. For example, a useful wettable powder formulation of the present invention contains about 80.0 parts of a compound of formula (I), about 17.9 parts of Palmetto clay, about 1.0 part of sodium lignosulfonate and 0.3 part of sulfonated aliphatic polyester as wetting agents.

Additional wetting agent and/or oil will frequently be added to the tank mix for post-emergence application to facilitate dispersion on the foliage and absorption by the plant.

Other useful formulations of the present invention for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these ECs are dispersed in water or other liquid carrier and normally applied as a spray to the area to be treated. The percentage by weight of the compound of formula (I) may vary according to the manner in which the composition is to be applied, but in general comprises about 0.5 to 95% by weight of the herbicidal composition.

Flowable formulations are similar to ECs except that the compound of formula (I) is suspended in a liquid carrier, generally water. Flowables, like ECs, may include a small amount of a surfactant, and will typically contain a compound of formula (I) in the range of about 0.5 to 95%, frequently, from about 10 to 50% by weight of the composition. For application, flowables may be diluted in water or other liquid vehicle, and are normally applied as a spray to the area to be treated.

Typical wetting, dispersing or emulsifying agents which may be used include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, may generally comprise about 1 to 15% by weight of the composition.

Other useful formulations include suspensions of the compound of formula (I) in a relatively non-volatile solvent such as water, corn oil, kerosene, propylene glycol, or other suitable solvents.

Still other useful formulations for herbicidal applications include simple solutions of the compound of formula (I) in a solvent in which it is completely soluble at the desired concentration. Such solvents include acetone, alkylated naphthalenes, xylene, or other organic solvents. Granular formulations, wherein the compound of formula (I) is carried on relative coarse particles, are of particular utility for aerial distribution or for penetration of cover crop canopy. Pressurized sprays, typically aerosols wherein the compound of formula (I) is dispersed in finely divided form as a result of vaporization of a low-boiling dispersant solvent carrier (such as fluorinated hydrocarbons (e.g., Freon®)), may also be used. Water-soluble or water-dispersible granules are free-flowing, non-dusty, and readily water-soluble or water-miscible. The soluble or dispersible granular formulations described in U.S. Pat. No. 3,920,442 may be used with the compound of formula (I). In use by the farmer on the field, the granular formulations, ECs, flowable concentrates, solutions, etc., may be diluted with water to give a concentration of the compound of formula (I) in the range of about 0.1% or 0.2% to about 1.5% or 2% by weight.

The compounds of formula (I) may be formulated and/or applied with at least one other active ingredient. Such other active ingredients include other pesticides (e.g., other herbicides, insecticides, fungicides or nematicides), plant growth regulators, fertilizers, soil conditioners, or other agricultural chemicals. The compounds of formula (I) may also be used as effective soil sterilants as well as selective herbicides in agriculture. In applying the compound of formula (I), whether formulated alone or with other agricultural chemicals, an herbicidally effective amount and concentration is employed; the amount may be as low as, e.g. about 1 to 250 g/ha, preferably about 4 to 30 g/ha. For field use where there are greater losses of herbicide, higher application rates (e.g., four times the rates mentioned above) may be employed.

When the compounds of formula (I) are used in combination with one or more other herbicides, such other herbicides include, for example: N-(phosphonomethyl)-glycine ("glyphosate"); aryloxyalkanoic acids such as (2,4-dichlorophenoxy)-acetic acid ("2,4-D"), (4-chloro-2-methylphenoxy)acetic acid ("MCPA"), (+/−)-2-(4chloro-2-methylphenoxy) -propanoic acid ("MCPP"); ureas such as N,N-dimethyl-N'-[4-(1-methyl-ethyl)phenyl]urea ("isoproturon"); imidazolinones such as 2-[4,5-dihydro-4-methyl-4-(1-methyl-ethyl)-5-oxo-1H-imidazol-2-yl]-3-pyridine-carboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methyl-ethyl)-5-oxo-1H-imidazol-2-yl]-5-methyl-benzoic acid ("imazamethabenz"), (+/−)-2-[4,5-dihydro-4-methyl-4-(1-methyl-ethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzene -sulfonamide (achlorsulfuron"), 2-[[[[[(4,6-dimethoxy-2-pyrimidinyl)amino]-carbonyl]amino]sufonyl]methyl]benzoic acid ("bensulfuron"), 2-[[[[(4,6 -dimethoxy-2-pyrimidinyl)amino]carbonyl]-amino]sulfonyl]-1-methy-1H -pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl) amino]carbonyl]benzenesulfonamide ("triasulfuron"); 2-(4-aryloxyphenoxy)alkanoic acids such as (+/−)-2[4-[(6-chloro-2-benzoxazolyl) -oxy]phenoxy]propanoic acid (fenoxaprop"), (+/−)-2-[4[[5-(trifluoromethyl)-2--pyridinyl]oxy]phenoxy]propanoic acid ("fluazifop"), (+/−)-2-[4-(6chloro-2-quinoxalinyl)oxy]phenoxy]propanoic acid ("quizalofop"), and (+/−)-2-[(2,4-dichlorophenoxy) phenoxy]-propanoic acid ("diclofop"); benzothiadiazinones such as 3-(1-methylethyl)-1H-2,1,3-benzothia-diazin-4 (3H)-one-2,2-dioxide ("bentazone"); 2-chloroacetanilides such as N-(butoxymethyl)-2-chloro-N-(2,6-diethylphenyl) acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1 -methylethyl) acetamide ("dimethenamide"); arenecarboxylic acids such as 3,6-dichloro-2-methoxybenzoic acid ("dicamba"); and pyridyloxyacetic acids such as [(4-amino-3,5-dichloro-6-fluoro-2-pyridinyl)oxy]acetic acid ("fluroxypyr").

When the compounds of formula (I) are used in combination with one or more insecticides, the insecticides include, for example: organophosphate insecticides such as chlorpyrifos, diazinon, dimethoate, malathion, parathion-methyl, and terbufos; pyrethroid insecticides such as fenvalerate, deltamethrin, fenpropathrin, cyfluthrin, flucythrinate, alpha-cypermethrin, biphenthrin, resolved cyhalothrin, etofenprox, esfenvalerate, tralomehtrin, tefluthrin, cycloprothrin, betacyfluthrin, and acrinathrin; carbamate insecticides such as aldecarb, carbaryl, carbofuran, and methomyl; organochlorine insecticides such as endosulfan, endrin, heptachlor, and lindane; benzoylurea insecticides such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, and imidacioprid.

When the compounds of formula (I) are used in combination with one or more fungicides, the fungicides include, for example: benzimidazole fungicides such as benomyl, carbendazim, thiabendazole, and thiophanate-methyl; 1,2,4-triazole fungicides such as epoxyconazole, cyproconazole, flusilazole, flutriafol, propiconazole, tebuconazole, triadimefon, and triadimenol; substituted anilide fungicides such as metalaxyl, oxadixyl, procymidone, and vinclozolin; organophosphorus fungicides such as fosetyl, iprobenfos, pyrazophos, edifenphos, and tolclofos-methyl; morpholine fungicides such as fenpropimorph, tridemorph, and dodemorph; other systemic fungicides such as fenarimol, imazalil, prochloraz, tricyclazole, and triforine; dithiocarbamate fungicides such as mancozeb, maneb, propineb, zineb, and ziram; non-systemic fungicides such as chlorothalonil, dichlofluanid, dithianon, and iprodione, captan, dinocap, dodine, fluazinam, gluazatine, PCNB, pencycuron, quintozene, tricylamide, and validamycin; and inorganic fungicides such as copper and sulphur products.

When the compounds of formula (I) are used in combination with one or more nematicides, the nematicides include, for example: carbofuran, carbosulfan, turbufos, aldecarb, ethoprop, fenamphos, oxamyl, isazofos and cadusafos.

When the compounds of formula (I) are used in combination with one or more plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione and trinexapac-ethyl.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil and promote better pesticide and fertilizer incorporation. When the compounds of formula (I) are used in combination with one or more soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, bacillus, pseudomonas, azotobacter, azospirillum, rhizobium, and soil-borne cyanobacteria.

Fertilizers are plant food supplements which commonly contain nitrogen, phosphorus, and potassium. When the compounds of formula (I) are used in combination with one or more fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate.

The present invention is now described in more detail by reference to the following examples, but it should be understood that the invention is not to be construed as being limited thereto. Unless indicated otherwise, all parts, percentages or the like are by weight.

EXAMPLE 1

This example illustrates a method for the synthesis of a compound within the scope of formula (I), namely, 3-[7-chloro-2-(1-methylethyl)isoindolin-1-on-4-yl]-1-methyl-6-trifluoromethyl-2,4(1H,3H)-pyrimidinedione (Compound 3 from Table 1 below).

Step A Preparation of 2-(1-methylethyl)-4-nitroisoindolin-1-one

A stirred solution of 5.9 grams (0.030 mole) of methyl 2-methyl-3-nitrobenzoate and 5.3 grams (0.030 mole) of NBS in 120 mL of carbon tetrachloride was exposed to uv light for about 18 hours. The reaction mixture was cooled and filtered to remove a solid material. The filtrate was concentrated under reduced pressure to a residue. The residue was the intermediate methyl 2-bromomethyl-3-nitrobenzoate, as determined by NMR analysis. The intermediate 2-bromomethyl compound was slowly added to 60 mL of diethyl ether, and the resulting solution was in turn added dropwise to 40 mL of stirred 1-methylethylamine at 25° C. Upon completion of addition, the reaction mixture was stirred at 25° C. for about 18 hours. The reaction mixture was then concentrated under reduced pressure to remove excess 1-methylethylamine. The resultant solid was washed with aqueous dilute hydrochloric acid and dried, yielding 6.0 grams of subject compound, mp 150–152 C. The NMR spectrum was consistent with the proposed structure.

Step B Preparation of 4-amino-2-(1-methylethyl)isoindolin-1-one

A stirred mixture of 5.0 grams (0.022 mole) of 2-(1-methylethyl)-4-nitroisoindolin-1-one and 10 mL of water in 100 mL of HOAc was warmed to 50 C., and 5.0 grams of iron dust was slowly added. Upon completion of addition, the reaction mixture was stirred at 25 C. for about two hours, then it was filtered through diatomaceous earth. The filtrate was diluted with water and extracted with EtOAc. The organic layer was separated and dried with magnesium sulfate. The mixture was filtered, and the filtrate was concentrated under reduced pressure to a residue. The residue was purified by column chromatography on silica gel using mixtures of EtOAc and methylene chloride as eluants. The fractions containing product were combined and concentrated under reduced pressure, yielding 3.6 grams of subject compound. The NMR spectrum was consistent with the proposed structure.

Step C Preparation of 4-amino-7-chloro-2-(1-methylethyl)isoindolin-1-one

A solution of 2.8 grams (0.015 mole) of 4-amino-2-(1-methylethyl)isoindolin-1-one and 2.0 grams (0.015 mole) of NCS in 80 mL of DMF was stirred at 25° C. for about 18 hours. The reaction mixture was then poured into water, and the mixture was extracted repeatedly with diethyl ether. The combined extracts were dried with magnesium sulfate and filtered. The filtrate was concentrated under reduced pressure to a residue. The residue was purified by column chromatography on silica gel using mixtures of EtOAc and methylene chloride as eluants. The fractions containing product were combined and concentrated under reduced pressure, yielding about 1.0 gram of subject compound. The NMR spectrum was consistent with the proposed structure.

Step D Preparation of 3-[7-chloro-2-(1-methylethyl)isoindolin-1-on-4-yl]-6-trifluoromethyl-2,4(1H,3H)-pyrimidinedione A solution of 0.90 gram (0.004 mole) of 4-amino-7-chloro-2-(1-methylethylisoindolin-1-one in 80 mL of toluene was stirred, and 0.79 gram (0.004 mole) of trichloromethyl chloroformate was added. The reaction mixture was stirred at 25° C. for one hour, then it was heated at reflux for three hours. After this time, excess trichloromethyl chloroformate and toluene were removed by distillation, leaving intermediate [7-chloro-2-(1-methylethyl)isoindolin-1-on-4-yl] isocyanate as a residue.

In a separate reaction vessel, a stirred mixture of 0.16 gram (0.004 mole) of 60% sodium hydride in about 60 mL of dry THF was cooled to 0–5° C. and 0.73 gram (0.004 mole) of 3-amino-4,4,4-trifluoro-2-butenoate was added. The resultant solution was stirred for about 20 minutes, and the isocyanate prepared above was added dropwise. Upon completion of addition, the reaction mixture was stirred at 2° C. for about 18 hours. The reaction mixture was concentrated under reduced pressure to a residue. The residue was stirred in aqueous hydrochloric acid, and the resultant solid was collected by filtration, yielding 0.89 gram of subject compound, mp >250° C. The NMR spectrum was consistent with the proposed structure.

Step E Preparation of 3-[7-chloro-2-(1-methylethyl)isoindolin-1-on-4-yl]-1-methyl-6-trifluoromethyl-2,4(1H,3H)-pyrimidinedione A solution of 0.90 gram (0.0023 mole) of 3-[7-chloro-2-(1-methylethyl)-isoindolin-1-on-4-yl]-6-trifluoromethyl-2,4(1H,3H)-pyrimidinedione, 0.42 gram (0.0030 mole) of potassium carbonate, and 0.45 gram (0.0030 mole) of methyl iodide in 60 mL of DMF was stirred at 25 C. for about 18 hours. The reaction mixture was then poured into water and extracted with diethyl ether. The organic layer was dried with magnesium sulfate, filtered, and concentrated under reduced pressure to a residue. The residue was purified by column chromatography on silica gel using mixtures of methylene chloride and EtOAc as eluants. The fractions containing product were combined and concentrated under reduced pressure, yielding about 0.65 gram of subject compound. The NMR spectrum was consistent with the proposed structure.

EXAMPLE 2

This example illustrates a method for the synthesis of a compound of formula (I), namely, 3-[7-chloro-2-(1,1-dimethylethyl)isoindolin-1-on-4-yl]-1-methyl-6-trifluoromethyl-2,4(1H,3H)-pyrimidinedione (Compound 14 from Table 1 below).

Step A Preparation of methyl 3-amino-2-methylbenzoate

In the presence of 0.1 gram of 5% palladium on carbon, a solution of 14.0 grams (0.072 mole) of methyl 2-methyl-3-nitrobenzoate in 100 mL of ethanol was hydrogenated using a Parr hydrogenator, yielding 11.6 grams of subject compound. The NMR spectrum was consistent with the proposed structure. The reaction was run several times.

Step B Preparation of methyl 3-amino-6-chloro-2-methylbenzoate

This compound was prepared in a manner analogous to Step C, Example 1. Here, 29.9 grams (0.181 mole) of methyl 3-amino-2-methylbenzoate was combined with 27.8 grams (0.208 mole) of NCS in 800 mL of DMF. The reaction product was purified by column chromatography on silica gel using mixtures of EtOAc and hexane as eluants. The fractions containing product were combined and concentrated under reduced pressure, yielding 14.7 grams of subject compound. The NMR spectrum was consistent with the proposed structure.

Step C Preparation of methyl 6-chloro-3-isocyanato-2-methylbenzoate

A solution of 14.7 grams (0.074 mole) of methyl 3-amino-6-chloro-2-methylbenzoate in 1000 mL of toluene was stirred and 14.6 grams (0.074 mole) of trichloromethyl chloroformate was added dropwise thereto. Upon completion of the addition, the reaction mixture was warmed to reflux where it stirred for about 18 hours. After this time the reaction mixture was concentrated under reduced pressure to a residue, which was assumed to be a theoretical yield (16.7 grams) of the subject compound. The subject compound was taken directly to the next reaction in the sequence.

Step D Preparation of methyl 6-chloro-2-methyl-3-[6-trifluoromethyl-2,4(1H,3H)-pyrimidinedion-3-yl]benzoate This compound was prepared in a manner analogous to the second part of Step D, Example 1. Here, 16.7 grams (0.074 mole) of methyl 6-chloro-3-isocyanato-2-methylbenzoate was combined with 4.4 grams (0.110 mole) of 60% sodium hydride and 14.2 grams (0.076 mole) of 3-amino-4,4,4-trifluoro-2-butenoate in 600 mL of THF. The reaction product was purified by column chromatography on silica using a 1:1 mixture of EtOAc and hexane as eluant. The fractions containing product were combined and concentrated under reduced pressure, yielding 15.8 grams of subject compound. The NMR spectrum was consistent with the proposed structure.

Step E Preparation of methyl 6-chloro-2-methyl-3-[1-methyl-6-trifluoromethyl-2,4(1H,3H)-pyrimidinedion-3-yl]benzoate This compound was prepared in a manner analogous to Step E, Example 1. Here, 8.2 grams (0.0206 mole) of methyl 6-chloro-2-methyl-3-[6-trifluoromethyl-2,4(1H,3H)-pyrimidinedion-3-yl]benzoate was combined with 5.7 grams (0.410 mole) of potassium carbonate and 4.4 grams (0.309 mole) of methyl iodide in 200 mL of THF. The reaction product was purified by column chromatography on silica gel using mixtures of EtOAc and hexane as eluants. The fractions containing product were combined and concentrated under reduced pressure, yielding 7.8 grams of subject compound. The NMR spectrum was consistent with the proposed structure.

Step F Preparation of methyl 2-bromomethyl-6-chloro-3-[1-methyl-6-trifluoromethyl-2,4(1H,3H)-pyrimidinedion-3-yl]benzoate A solution of 11.4 grams (0.030 mole) of methyl 6-chloro-2-methyl-3-[1-methyl-6-trifluoromethyl-2,4(1H,3H)-pyrimidinedion-3-yl]benzoate and 5.4 grams (0.030 mole) of NBS in the presence of 0.03 gram of benzoyl peroxide in 250 mL of carbon tetrachloride was irradiated with a sun lamp as it stirred at reflux for about 18 hours. The reaction mixture was then cooled and washed with water. The organic layer was dried with magnesium sulfate and filtered. The filtrate was concentrated under reduced pressure to a residue. The residue was subjected to NMR analysis, which indicated that the reaction was about 15% complete. The residue was recharged to the reaction vessel and treated with the same amounts of NBS, benzoyl peroxide, and carbon tetrachloride under the same conditions as described above. Upon completion of the second 18 hour reflux period, a small sample was washed with water, dried with magnesium sulfate and filtered. The filtrate was concentrated under reduced pressure to a residue. The residue was subjected to NMR analysis, which indicated that the reaction was about 70% complete. An additional 2.0 grams (0.011 mole) of NBS was added, and the solution was irradiated at reflux for an additional 18 hours. The reaction mixture was then cooled and washed with water. The organic layer was dried with magnesium sulfate, filtered, and concentrated under reduced pressure to a residue. The residue was purified by column chromatography on silica gel, and the fractions containing product were combined and concentrated under reduced pressure, yielding 11.0 grams of subject compound. The NMR spectrum was consistent with the proposed structure.

Step G Preparation of 3-[7-chloro-2-(1,1-dimethylethyl)isoindolin-1-on-4-yl]-1-methyl-6-trifluoromethyl-2,4(1H,3H)-pyrimidinedione A solution of 0.50 gram (0.0011 mole) of methyl 2-bromo-methyl-6-chloro-3-[1-methyl-6-trifluoromethyl-2,4(1H,3H)-pyrimidinedion-3-yl]benzoate and 0.18 gram (0.0025 mole) of tert.-butylamine in 50 mL of THF was stirred at ambient temperature for about 18 hours. After this time, TLC analysis of the reaction mixture indicated little reaction had taken place. The reaction mixture was warmed to reflux where it stirred for an additional 18 hours, then it was concentrated under reduced pressure to a residue. The residue was taken up in methylene chloride and washed in turn with water and an aqueous solution saturated with sodium chloride. The organic layer was dried with magnesium sulfate and filtered. The filtrate was concentrated under reduced pressure to a residue. The residue was purified by column chromatography on silica gel using mixtures of EtOAc and hexane as eluants. The fractions containing product were combined and concentrated under reduced pressure, yielding 0.36 gram of subject compound. The NMR spectrum was consistent with the proposed structure.

EXAMPLE 3

This example illustrates a method for the synthesis of a compound of formula (I), namely, 1-[5,7-dichloro-2-(1-methylethyl)isoindolin-1-on-4-yl]-3,4,5,6-tetrahydrophthalimide (Compound 82 as set forth in Table 1 below).

A stirred solution of 1.0 gram (0.004 mole) of 4-amino-5,7-dichloro-2-(1-methylethyl)isoindolin-1-one (prepared in a manner analogous to Steps A–C of Example 1) and 0.6 gram (0.004 mole) of 3,4,5,6-tetrahydrophthalic anhydride in 60 mL of HOAc was heated at reflux for about 18 hours. TLC analysis of the reaction mixture indicated that the reaction was not complete. An additional 0.2 gram of 3,4,5,6-tetrahydrophthalic anhydride was added to the reaction mixture, which was then heated at reflux for about 18 additional hours. The reaction mixture was cooled and concentrated under reduced pressure to a residue. The residue was dissolved in EtOAc and washed with water. The organic layer was dried with magnesium sulfate and filtered. The filtrate was concentrated under reduced pressure to a residue. The residue was purified by column chromatography on silica gel using mixtures of methylene chloride and EtOAc as eluants. The fractions containing product were combined and concentrated under reduced pressure, yielding 0.55 gram of subject compound, mp 120–124° C. The NMR spectrum was consistent with the proposed structure.

EXAMPLE 4

This example illustrates a method for the synthesis of a compound of formula (I), namely, 2-[7-chloro-2-(1- methylethyl)isoindolin-1-on-4-yl]-5,6,7,8-tetrahydro-1,2,4-triazolo[4,3-A]pyridin-3(2H)-one (Compound 83 as set forth in Table 1 below).

Step A Preparation of [7-chloro-2-(1-methylethyl)isoindolin-1-on-4-yl]hydrazine hydrochloride A stirred solution of 4.0 grams (0.018 mole) of 4-amino-7-chloro-2-(1-methylethyl)isoindolin-1-one in 40 mL of concentrated hydrochloric acid was cooled in an ice-water bath, and a solution of 1.2 grams (0.018 mole) of sodium nitrite in 20 mL of water was added dropwise while maintaining the reaction mixture temperature under 5° C. Upon completion of addition, the reaction mixture was stirred for about 45 minutes, then a solution of 8.8 grams (0.039 mole) of tin(II) chloride in 20 mL of concentrated hydrochloric acid was added dropwise while still maintaining the reaction mixture temperature under 5° C. After this time the reaction mixture was stirred for about one hour at 5° C., then it was filtered to collect, after drying, 4.6 grams of subject compound, mp 186° C., dec. The NMR spectrum was consistent with the proposed structure.

Step B Preparation of (aza-2-piperidylidenemethyl)[7-chloro-2-(1-methylethyl)isoindolin-1-on-4-yl]amine A stirred solution of 4.3 grams (0.016 mole) of [7-chloro-2-(1-methylethyl)isoindolin-1-on-4-yl]hydrazine hydrochloride and 10 mL of methanol in 40 mL of HOAc was cooled in an ice-water bath and 2.6 grams (0/023 mole) of O-methylvalerolactin was added dropwise, followed by 0.5 gram (catalyst) of concentrated sulfuric acid. Upon completion of addition, the reaction mixture was allowed to warm to ambient temperature where it stirred for about 18 hours. After this time the reaction mixture was cooled, cold aqueous 10% sodium hydroxide was added, and the mixture was extracted with EtOAc. The combined extracts were washed with water, then with aqueous concentrated sodium chloride solution. The organic layer was dried with magnesium sulfate and filtered. The filtrate was concentrated under reduced pressure to a residue. The residue was purified by column chromatography on silica gel using mixtures of EtOAc, hexane, and methanol as eluants. The fractions containing product were combined and concentrated under reduced pressure, yielding 1.4 grams of subject compound. The NMR spectrum was consistent with the proposed structure.

Step C Preparation of 2-[7-chloro-2-(1-methylethyl)isoindolin-1-on-4-yl]-5,6,7,8-tetrahydro-1,2,4-triazolo[4,3-A]pyridin-3(2H)-one A stirred solution of 1.4 grams (0.004 mole) of (aza-2-piperidyl-idenemethyl)[7-chloro-2-(1-methylethyl)isoindolin-1-on-4-yl]amine in about 25 mL of THF was cooled to −40 C. and 3.5 mL (0.009 mole) of n-butyllithium (2.5M in hexane) was added dropwise. Upon completion of addition, the reaction mixture was stirred for 30 minutes, then a solution of 0.5 gram (0.005 mole) of ethyl chloroformate in about five mL of THF was added dropwise. Upon completion of addition, the reaction mixture was allowed to warm to ambient temperature where it stirred for about 18 hours. After this time the reaction mixture was poured into aqueous 1N hydrochloric acid. The mixture was extracted with EtOAc, and the extract was washed with water, then with aqueous concentrated sodium chloride solution. The organic layer was dried with sodium sulfate and filtered. The filtrate was concentrated under reduced pressure to a residue. The residue was purified by column chromatography on silica gel using mixtures of EtOAc, hexane, and methanol as eluants. The fractions containing product were combined and concentrated under reduced pressure, yielding 0.1 gram of subject compound. The NMR spectrum was consistent with the proposed structure.

EXAMPLE 5

The following compounds are representative of compounds of formula (I) and can be made using the methods of Examples 1–4:

TABLE 1

| Cmpd No | X | Y | n | Q | R | $R_1$ |
|---|---|---|---|---|---|---|
| 1 | H | Cl | 1 | Q1 | $CH(CH_3)_2$ | $CH_3$ |
| 2 | Cl | H | 1 | Q1 | $CH(CH_3)_2$ | H |
| 3 | Cl | H | 1 | Q1 | $CH(CH_3)_2$ | $CH_3$ |
| 4 | Cl | Cl | 1 | Q1 | $CH(CH_3)_2$ | $CH_3$ |
| 5 | Cl | Cl | 1 | Q1 | $C_2H_5$ | $CH_3$ |
| 6 | Cl | Cl | 1 | Q1 | $C(CH_3)_3$ | $CH_3$ |
| 7 | Cl | H | 1 | Q1 | $CH_2CO_2C_2H_5$ | $CH_3$ |
| 8 | Cl | H | 1 | Q1 | $CH_2C\equiv CH$ | $CH_3$ |
| 9 | Cl | H | 1 | Q1 | $CH_3$ | $CH_3$ |
| 10 | Cl | H | 1 | Q1 | $CH_2Ph$ | $CH_3$ |
| 11 | Cl | H | 1 | Q1 | $C_4H_9$ | $CH_3$ |
| 12 | Cl | H | 1 | Q1 | H | $CH_3$ |
| 13 | Cl | H | 1 | Q1 | $C_3H_7$ | $CH_3$ |
| 14 | Cl | H | 1 | Q1 | $C(CH_3)_3$ | $CH_3$ |
| 15 | Cl | Cl | 1 | Q1 | H | $CH_3$ |
| 16 | Cl | Cl | 1 | Q1 | OH | $CH_3$ |
| 17 | Cl | H | 1 | Q1 | $OCH_2CH=CH_2$ | $CH_3$ |
| 18 | Cl | H | 1 | Q1 | OH | $CH_3$ |
| 19 | Cl | H | 1 | Q1 | $OC_2H_5$ | $CH_3$ |
| 20 | Cl | H | 1 | Q1 | $CH_2CH=CH_2$ | $CH_3$ |
| 21 | Cl | H | 1 | Q1 | $OCH_3$ | $CH_3$ |
| 22 | Cl | H | 1 | Q1 | $C_2H_5$ | $CH_3$ |
| 23 | Cl | H | 1 | Q1 | $C_2H_4OCH_3$ | $CH_3$ |
| 24 | Cl | H | 1 | Q1 | $CH_2Ph$; 4-Cl | $CH_3$ |
| 25 | Cl | H | 1 | Q1 | $CH_2Ph$; 4-$OCH_3$ | $CH_3$ |
| 26 | Cl | H | 1 | Q1 | $C_2H_4CO_2CH_3$ | $CH_3$ |
| 27 | Cl | H | 1 | Q1 | $NH_2$ | $CH_3$ |
| 28 | Cl | H | 1 | Q1 | $CH_2CF_3$ | $CH_3$ |
| 29 | Cl | H | 1 | Q1 | $CH_2$-cyclopropyl | $CH_3$ |
| 30 | Cl | H | 1 | Q1 | $CH_2C\equiv N$ | $CH_3$ |
| 31 | Cl | H | 1 | Q1 | $CH_2OCH_3$ | $CH_3$ |
| 32 | Cl | F | 1 | Q1 | H | $CH_3$ |
| 33 | Cl | F | 1 | Q1 | $CH_3$ | $CH_3$ |
| 34 | Cl | F | 1 | Q1 | $C_2H_5$ | $CH_3$ |
| 35 | Cl | F | 1 | Q1 | $C_3H_7$ | $CH_3$ |
| 36 | Cl | F | 1 | Q1 | $CH(CH_3)_2$ | $CH_3$ |
| 37 | Cl | F | 1 | Q1 | $C_2H_4F$ | $CH_3$ |
| 38 | Cl | F | 1 | Q1 | $CH_2C\equiv N$ | $CH_3$ |
| 39 | Cl | F | 1 | Q1 | $CH_2CO_2C_2H_5$ | $CH_3$ |
| 40 | Cl | F | 1 | Q1 | $CH_2OCH_3$ | $CH_3$ |
| 41 | Cl | F | 1 | Q1 | $C(CH_3)_3$ | $CH_3$ |
| 42 | Cl | F | 1 | Q1 | OH | $CH_3$ |
| 43 | Cl | F | 1 | Q1 | $OCH_3$ | $CH_3$ |
| 44 | Cl | F | 1 | Q1 | $OCH_2CH=CH_2$ | $CH_3$ |
| 45 | Cl | F | 1 | Q1 | $CH_2C\equiv CH$ | $CH_3$ |
| 46 | Cl | F | 1 | Q1 | $CH_2CH=CH_2$ | $CH_3$ |
| 47 | Cl | F | 1 | Q1 | $CH_2Ph$ | $CH_3$ |
| 48 | Cl | F | 1 | Q1 | $CH(CH_3)_2$ | H |
| 49 | Cl | F | 1 | Q1 | $CH(CH_3)_2$ | $NH_2$ |
| 50 | Cl | F | 1 | Q1 | $CH(CH_3)_2$ | $C_2H_5$ |
| 51 | Cl | F | 1 | Q1 | $CH(CH_3)_2$ | $C_3H_7$ |
| 52 | Cl | F | 1 | Q1 | $CH(CH_3)_2$ | $CH(CH_3)_2$ |
| 53 | Cl | F | 1 | Q1 | $CH(CH_3)_2$ | $CH_2C\equiv N$ |
| 54 | Cl | F | 1 | Q1 | $CH(CH_3)_2$ | $CH_2CO_2C_2H_5$ |
| 55 | Cl | F | 1 | Q1 | $CH(CH_3)_2$ | $CH_2CH=CH_2$ |
| 56 | Cl | F | 1 | Q1 | $CH(CH_3)_2$ | $CH_2C\equiv CH$ |
| 57 | Cl | F | 1 | Q1 | $CH(CH_3)_2$ | $CH_2OCH_3$ |
| 58 | Cl | F | 1 | Q1 | $CH(CH_3)_2$ | $CHF_2$ |
| 59 | Cl | F | 1 | Q1 | $CH(CH_3)_2$ | $C_3H_9F$ |
| 60 | Cl | F | 1 | Q1 | $CH(CH_3)_2$ | $CH_2Ph$ |
| 61 | Cl | F | 1 | Q1 | $CH(CH_3)_2$ | Na |
| 62 | $NO_2$ | F | 1 | Q1 | $CH(CH_3)_2$ | $CH_3$ |
| 63 | $C\equiv N$ | F | 1 | Q1 | $CH(CH_3)_2$ | $CH_3$ |
| 64 | $CF_3$ | F | 1 | Q1 | $CH(CH_3)_2$ | $CH_3$ |
| 65 | Cl | F | 1 | Q2 | $CH(CH_3)_2$ | — |
| 66 | Cl | F | 1 | Q3 | $CH(CH_3)_2$ | — |
| 67 | Cl | F | 1 | Q4 | $CH(CH_3)_2$ | — |
| 68 | Cl | F | 1 | Q5 | $CH(CH_3)_2$ | — |
| 69 | Cl | F | 1 | Q6 | $CH(CH_3)_2$ | — |
| 70 | Cl | H | 1 | Q1 | $CH(CH_3)_2$ | $NH_2$ |

TABLE 1-continued

| Cmpd No | X | Y | n | Q | R | R₁ |
|---|---|---|---|---|---|---|
| 71 | Cl | H | 1 | Q1 | $CH(CH_3)_2$ | $C_2H_5$ |
| 72 | Cl | H | 1 | Q1 | $CH(CH_3)_2$ | $C_3H_7$ |
| 73 | Cl | H | 1 | Q1 | $CH(CH_3)_2$ | $CH_2Ph$ |
| 74 | Cl | H | 1 | Q1 | $CH(CH_3)_2$ | $CH_2CO_2C_2H_5$ |
| 75 | Cl | H | 1 | Q1 | $CH(CH_3)_2$ | $CH_2C{\equiv}CH$ |
| 76 | Cl | H | 1 | Q1 | cyclopentyl | $CH_3$ |
| 77 | Cl | H | 1 | Q1 | cyclohexyl | $CH_3$ |
| 78 | Cl | H | 1 | Q1 | $C_2H_4F$ | $CH_3$ |
| 79 | Cl | H | 1 | Q1 | $CH(CH_3)_2$ | $C_3H_6F$ |
| 80 | Cl | H | 1 | Q1 | $CH(CH_3)_2$ | $CH_2CH{=}CH_2$ |
| 81 | Br | H | 1 | Q1 | $CH(CH_3)_2$ | $CH_3$ |
| 82 | Cl | Cl | 1 | Q1 | $CH(CH_3)_2$ | — |
| 83 | Cl | H | 1 | Q4 | $CH(CH_3)_2$ | — |
| 84 | Cl | H | 1 | Q2 | $CH(CH_3)_2$ | — |
| 85 | F | H | 1 | Q1 | $CH(CH_3)_2$ | $CH_3$ |
| 86 | F | F | 1 | Q1 | $CH(CH_3)_2$ | $CH_3$ |
| 87 | $OCHF_2$ | H | 1 | Q1 | $CH(CH_3)_2$ | $CH_3$ |
| 88 | $OCH_3$ | H | 1 | Q1 | $CH(CH_3)_2$ | $CH_3$ |
| 89 | $CH_3$ | H | 1 | Q1 | $CH(CH_3)_2$ | $CH_3$ |
| 90 | Cl | Br | 1 | Q1 | $CH(CH_3)_2$ | $CH_3$ |
| 91 | Br | Br | 1 | Q1 | $CH(CH_3)_2$ | $CH_3$ |
| 92 | Cl | $CH_3$ | 1 | Q1 | $CH(CH_3)_2$ | $CH_3$ |
| 93 | Cl | $CF_3$ | 1 | Q1 | $CH(CH_3)_2$ | $CH_3$ |
| 94 | Cl | F | 1 | Q7 | $CH(CH_3)_2$ | |
| 95 | Cl | F | 1 | Q8 | $CH(CH_3)_2$ | |
| 96 | Cl | F | 1 | Q9 | $CH(CH_3)_2$ | |
| 97 | Cl | F | 1 | Q10 | $CH(CH_3)_2$ | |
| 98 | Cl | F | 1 | Q11 | $CH(CH_3)_2$ | |
| 99 | Cl | F | 1 | Q12 | $CH(CH_3)_2$ | |
| 100 | Cl | H | 2 | Q1 | $CH(CH_3)_2$ | |
| 101 | Cl | F | 2 | Q1 | $CH(CH_3)_2$ | |
| 102 | Cl | F | 2 | Q2 | $CH(CH_3)_2$ | |
| 103 | Cl | F | 2 | Q3 | $CH(CH_3)_2$ | |
| 104 | Cl | F | 2 | Q4 | $CH(CH_3)_2$ | |
| 105 | Cl | F | 2 | Q5 | $CH(CH_3)_2$ | |
| 106 | Cl | F | 2 | Q6 | $CH(CH_3)_2$ | |
| 107 | Cl | F | 2 | Q7 | $CH(CH_3)_2$ | |
| 108 | Cl | F | 2 | Q8 | $CH(CH_3)_2$ | |
| 109 | Cl | F | 2 | Q9 | $CH(CH_3)_2$ | |
| 110 | Cl | F | 2 | Q10 | $CH(CH_3)_2$ | |
| 111 | Cl | F | 2 | Q11 | $CH(CH_3)_2$ | |
| 112 | Cl | F | 2 | Q12 | $CH(CH_3)_2$ | |

Observations were made relative to the physical characteristics of certain compounds of the present invention. Melting point determinations, where feasible, were conducted using standard procedures. These data are provided below:

TABLE 2

| Cmpd No | Melting Point (° C.) | Cmpd No | Melting Point (° C.) | Cmpd No | Melting Point (° C.) |
|---|---|---|---|---|---|
| 1 | 178–179 | 2 | 243–245 | 3 | 177–180 |
| 4 | Oil | 5 | Oil | 6 | 110–113 |
| 7 | Oil | 8 | 193–194 | 9 | Solid |
| 10 | Oil | 11 | 185–186 | 12 | >250 |
| 13 | Solid | 14 | Oil | 15 | >250 |
| 16 | 174–177 | 17 | Oil | 18 | 160–163 |
| 19 | Oil | 20 | 138–140 | 21 | Oil |
| 22 | 128–133 | 23 | Oil | 24 | 182–184 |
| 25 | Oil | 26 | Oil | 27 | Gummy solid |
| 28 | Amorphous solid | 29 | Oil | 30 | Amorphous solid |
| 31 | Oil | 70 | Gummy solid | 71 | Oil |
| 72 | Oil | 73 | Oil | 74 | Oil |
| 75 | Amorphous solid | 76 | Oil | 77 | Oil |
| 78 | Oil | 79 | Oil | 80 | Oil |
| 81 | Solid | 82 | 120–124 | 83 | 170–174 |

EXAMPLE 6

The following compounds are representative of compounds of formulas (II) and (III).

TABLE 3

Compounds of formula (II)

| Cmpd. No. | X | Y | n | R | Cmpd. No. | X | Y | n | R |
|---|---|---|---|---|---|---|---|---|---|
| 113 | H | H | 1 | $CH_3$ | 114 | H | H | 1 | $C_2H_5$ |
| 115 | H | H | 1 | $C_3H_7$ | 116 | H | H | 1 | $CH(CH_3)_2$ |
| 117 | Cl | H | 1 | $CH_3$ | 118 | Cl | H | 1 | $C_2H_5$ |
| 119 | Cl | H | 1 | $C_3H_7$ | 120 | Cl | H | 1 | $CH(CH_3)_2$ |
| 121 | H | F | 1 | $CH(CH_3)_2$ | 122 | Cl | F | 1 | $CH(CH_3)_2$ |
| 123 | Cl | Cl | 1 | $CH(CH_3)_2$ | 124 | H | H | 2 | $CH(CH_3)_2$ |
| 125 | Cl | H | 2 | $CH(CH_3)_2$ | 126 | Cl | Cl | 2 | $CH(CH_3)_2$ |
| 127 | H | F | 2 | $CH(CH_3)_2$ | 128 | Cl | F | 2 | $CH(CH_3)_2$ |

Compounds of formula (III)

| Cmpd. No. | X | Y | $R_2$ | Q | Cmpd. No. | X | Y | $R_2$ | Q |
|---|---|---|---|---|---|---|---|---|---|
| 129 | Cl | H | $CH_3$ | Q1 | 130 | Cl | H | $CH_3$ | Q2 |
| 131 | Cl | H | $CH_3$ | Q3 | 132 | Cl | H | $CH_3$ | Q4 |
| 133 | Cl | H | $CH_3$ | Q5 | 134 | Cl | H | $CH_3$ | Q6 |
| 135 | Cl | H | $CH_3$ | Q7 | 136 | Cl | H | $CH_3$ | Q8 |
| 137 | Cl | H | $CH_3$ | Q9 | 138 | Cl | H | $CH_3$ | Q10 |
| 139 | Cl | H | $CH_3$ | Q11 | 140 | Cl | H | $CH_3$ | Q12 |
| 141 | Cl | H | $CH_2Br$ | Q1 | 142 | Cl | H | $CH_2Br$ | Q2 |
| 143 | Cl | H | $CH_2Br$ | Q3 | 144 | Cl | H | $CH_2Br$ | Q4 |
| 145 | Cl | H | $CH_2Br$ | Q5 | 146 | Cl | H | $CH_2Br$ | Q6 |
| 147 | Cl | H | $CH_2Br$ | Q7 | 148 | Cl | H | $CH_2Br$ | Q8 |
| 149 | Cl | H | $CH_2Br$ | Q9 | 150 | Cl | H | $CH_2Br$ | Q10 |
| 151 | Cl | H | $CH_2Br$ | Q11 | 152 | Cl | H | $CH_2Br$ | Q12 |

EXAMPLE 7

This example sets forth the methods of herbicidal testing conducted on the specific compounds set forth below. Specifically, the compounds referenced below were tested for pre- and post-emergence herbicidal activity using a variety of crops and weeds. The test plants include, but are not limited to, soybean (*Glycine max* __ var. Winchester), field corn (*Zea mays* var. Pioneer 3732), wheat (*Triticum aestivum* var. Lew), morningglory (*Ipomea lacunosa* or *Ipomea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium strumarium* L.).

In the post-emergence test, seeds of the plant species named above were planted in flats containing the appropriate soil mixture where they were maintained to allow the seeds to germinate. When the plants in these flats reached the proper stage of growth, flats for the pre-emergence tests were planted in a like manner. The flats containing the post-emergence and pre-emergence test plant species were then sprayed with an appropriately concentrated water/ acetone solution of test compound. Once treated the flats were maintained, along with untreated controls, for about fourteen days. All treated plants were then examined for phytotoxicity, which was expressed as percent control where 0 is no effect and 100 is complete control. Effective rates of application for the compounds of the present invention range from 0.001 to 3 kg/ha, more likely from 0.0003 to 1 Kg/ha.

Herbicidal activity data at selected application rates are in Tables 4 and 5. The test compounds are identified by numbers correspond to those in Table 1.

TABLE 4

PRE-EMERGENCE HERBICIDAL ACTIVITY (% CONTROL)

| Cmpd No | SOY | WHT | CRN | ABUTH | IPOSS | STEME | XANPE | ALOMY | SETVI | SORHA |
|---|---|---|---|---|---|---|---|---|---|---|
| 1 | 90 | 80 | 95 | 100 | 100 | 90 | 70 | 80 | 100 | 90 |
| 3 | 100 | 100 | 100 | 100 | 100 | 100 | 100 | 100 | 100 | 100 |
| 4 | 100 | 100 | 100 | 100 | 100 | 100 | 100 | 100 | 100 | 100 |
| 5 | 100 | 100 | 100 | 100 | 100 | 100 | 100 | 100 | 100 | 100 |
| 6 | 100 | 100 | 100 | 100 | 100 | 100 | 100 | 100 | 100 | 100 |
| 7 | 70 | 30 | 70 | 100 | 80 | 60 | 50 | 40 | 70 | 55 |
| 8 | 100 | 100 | 100 | 100 | 100 | 100 | 100 | 100 | 100 | 100 |
| 9 | 100 | 100 | 100 | 100 | 100 | 100 | 100 | 100 | 100 | 100 |
| 10 | 80 | 70 | 90 | 100 | 80 | 100 | 80 | 80 | 100 | 100 |
| 11 | 100 | 100 | 100 | 100 | 100 | 100 | 100 | 100 | 100 | 100 |
| 12 | 100 | 100 | 100 | 100 | 100 | 100 | 100 | 100 | 100 | 100 |
| 13 | 100 | 100 | 100 | 100 | 100 | 100 | 100 | 100 | 100 | 100 |
| 14 | 100 | 100 | 100 | 100 | 100 | 100 | 100 | 100 | 100 | 100 |
| 15 | 100 | 95 | 95 | 100 | 100 | 60 | 100 | 100 | 100 | 100 |
| 16 | 50 | 70 | 90 | 100 | 65 | 5 | 80 | 60 | 100 | 100 |
| 17 | 100 | 100 | 100 | 100 | 100 | 100 | 100 | ND | 100 | 100 |
| 18 | 95 | 60 | 100 | 100 | 100 | ND | 100 | ND | 100 | 100 |
| 19 | 100 | 100 | 100 | 100 | 100 | 100 | 100 | ND | 100 | 100 |
| 20 | 100 | 100 | 100 | 100 | 100 | 100 | 100 | ND | 100 | 100 |
| 21 | 100 | 100 | 100 | 100 | 100 | 100 | 100 | ND | 100 | 100 |
| 22 | 100 | 100 | 100 | 100 | 100 | 100 | 100 | ND | 100 | 100 |
| 23 | 100 | 100 | 100 | 100 | 100 | 100 | 100 | ND | 100 | ND |
| 24 | 10 | 30 | 50 | 100 | 30 | 70 | 10 | ND | 95 | ND |
| 25 | 50 | 60 | 95 | 100 | 70 | 100 | 40 | 75 | 100 | ND |
| 26 | 100 | 50 | 80 | 100 | 80 | 100 | 100 | 80 | 80 | ND |
| 28 | 100 | 100 | 100 | 100 | 100 | 100 | 100 | 100 | 100 | ND |
| 29 | 100 | 100 | 100 | 100 | 100 | 100 | 100 | 100 | 100 | ND |
| 30 | 100 | 100 | 100 | 100 | 100 | 100 | 100 | 100 | 100 | ND |
| 31 | 100 | 100 | 100 | 100 | 100 | 100 | 100 | 100 | 100 | ND |
| 70 | 100 | 100 | 100 | 100 | 100 | 100 | 100 | 100 | 100 | ND |
| 71 | 100 | 100 | 100 | 100 | 100 | 100 | 100 | 90 | 100 | ND |
| 72 | 20 | 30 | 70 | 40 | 25 | 65 | 40 | 30 | 75 | ND |
| 73 | 95 | 69 | 90 | 100 | 40 | 100 | 70 | 70 | 100 | ND |
| 74 | 5 | 0 | 0 | 5 | 20 | 10 | 30 | 10 | 5 | ND |
| 75 | 100 | 100 | 95 | 100 | 100 | 100 | 95 | 95 | 100 | ND |
| 76 | 100 | 80 | 95 | 100 | 100 | 100 | 100 | 90 | 100 | ND |
| 77 | 100 | 80 | 90 | 100 | 100 | 100 | 100 | 95 | 100 | ND |
| 78 | 100 | 100 | 100 | 100 | 100 | 100 | 100 | 100 | 100 | ND |
| 79 | 50 | 60 | 90 | 95 | 100 | 70 | 30 | 70 | 100 | ND |
| 80 | 70 | 80 | 70 | 100 | 80 | 100 | 40 | 80 | 95 | ND |
| 81 | 100 | 100 | 100 | 100 | 100 | 100 | 100 | 100 | 100 | ND |
| 82 | 70 | 60 | 80 | 100 | 100 | 100 | 95 | 70 | 100 | ND |
| 83 | 5 | 10 | 0 | 100 | 60 | 100 | 30 | 50 | 60 | ND |

Rate of application of test compound is 1 kg/Ha
ND is no data
SOY is soybean, WHT is wheat, CRN is corn, ABUTH is velvetleaf, IPOSS is morningglory, STEME is chickweed, XANPE is cocklebur, ALOMY is blackgrass, SETVI is green foxtail, and SORHA is johnsongrass

TABLE 5

POST-EMERGENCE HERBICIDAL ACTIVITY (% CONTROL)

| Cmpd No | SOY | WHT | CRN | ABUTH | IPOSS | STEME | XANPE | ALOMY | SETVI | SORHA |
|---|---|---|---|---|---|---|---|---|---|---|
| 1 | 95 | 70 | 90 | 100 | 70 | 50 | 60 | 75 | 80 | 100 |
| 3 | 95 | 100 | 100 | 100 | 100 | 100 | 100 | 100 | 100 | 100 |
| 4 | 100 | 100 | 100 | 100 | 100 | 100 | 100 | 100 | 100 | 100 |
| 5 | 95 | 100 | 100 | 100 | 100 | 100 | 100 | 100 | 100 | 100 |
| 6 | 90 | 80 | 100 | 100 | 95 | 100 | 100 | 100 | 100 | 100 |
| 7 | 60 | 20 | 40 | 80 | 40 | ND | 60 | ND | 60 | 40 |
| 8 | 100 | 100 | 100 | 100 | 100 | ND | 100 | ND | 100 | 100 |
| 9 | 100 | 50 | 50 | 100 | 90 | ND | 70 | ND | 70 | 50 |

TABLE 5-continued

POST-EMERGENCE HERBICIDAL ACTIVITY (% CONTROL)

| Cmpd No | SOY | WHT | CRN | ABUTH | IPOSS | STEME | XANPE | ALOMY | SETVI | SORHA |
|---|---|---|---|---|---|---|---|---|---|---|
| 10 | 65 | 40 | 60 | 100 | 40 | ND | 50 | ND | 60 | 40 |
| 11 | 95 | 100 | 80 | 100 | 95 | ND | 100 | ND | 100 | 90 |
| 12 | 95 | 70 | 70 | 100 | 75 | ND | 95 | ND | 100 | 60 |
| 13 | 100 | 100 | 100 | 100 | 100 | ND | 95 | ND | 100 | 100 |
| 14 | 100 | 100 | 80 | 100 | 90 | ND | 100 | ND | 100 | 100 |
| 15 | 70 | 50 | 60 | 100 | 100 | ND | 60 | ND | 60 | 40 |
| 16 | 60 | 20 | 40 | 50 | 20 | ND | 30 | ND | 30 | 30 |
| 17 | 100 | 100 | 90 | 100 | 90 | ND | 100 | ND | 100 | 100 |
| 18 | 80 | 50 | 70 | 100 | 100 | ND | 95 | ND | 70 | 65 |
| 19 | 100 | 100 | 100 | 100 | 100 | 100 | 100 | ND | 100 | 100 |
| 20 | 100 | 100 | 100 | 100 | 100 | 100 | 100 | ND | 100 | 100 |
| 21 | 100 | 80 | 80 | 100 | 100 | 100 | 95 | ND | 100 | 100 |
| 22 | 100 | 100 | 100 | 100 | 100 | 100 | 100 | ND | 100 | 100 |
| 23 | 100 | 100 | 80 | 100 | 100 | 100 | 100 | 100 | 100 | 100 |
| 24 | 60 | 30 | 70 | 100 | 30 | 100 | 80 | 70 | 70 | 40 |
| 25 | 80 | 40 | 90 | 100 | 90 | 80 | 60 | ND | 100 | 75 |
| 26 | 100 | 70 | 95 | 100 | 80 | 100 | 100 | ND | 100 | 80 |
| 28 | 100 | 100 | 100 | 100 | 100 | 100 | 100 | ND | 100 | 100 |
| 29 | 100 | 100 | 100 | 100 | 100 | 100 | 100 | ND | 100 | 100 |
| 30 | 100 | 60 | 95 | 100 | 100 | 100 | 100 | ND | 100 | 100 |
| 31 | 100 | 100 | 100 | 100 | 100 | 100 | 100 | ND | 100 | 100 |
| 70 | 100 | 100 | 100 | 100 | 100 | 100 | 100 | ND | 100 | 100 |
| 71 | 90 | 80 | 90 | 95 | 95 | 100 | 70 | 100 | 100 | ND |
| 72 | 60 | 0 | 60 | 20 | 10 | 10 | 10 | 10 | 50 | ND |
| 73 | 90 | 50 | 75 | 100 | 80 | 100 | 75 | 70 | 60 | ND |
| 74 | 40 | 10 | 30 | 20 | 30 | 20 | 20 | 30 | 10 | ND |
| 75 | 60 | 70 | 50 | 100 | 50 | 100 | 85 | 100 | 45 | ND |
| 76 | 95 | 100 | 100 | 100 | 100 | 100 | 100 | 100 | 100 | ND |
| 77 | 95 | 80 | 100 | 100 | 100 | 100 | 100 | 100 | 100 | ND |
| 78 | 100 | 100 | 100 | 100 | 100 | 100 | 100 | 100 | 100 | ND |
| 79 | 80 | 30 | 60 | 80 | 30 | ND | 30 | 50 | 60 | ND |
| 80 | 85 | 50 | 75 | 95 | 30 | 100 | 40 | 65 | 80 | ND |
| 81 | 100 | 100 | 100 | 100 | 100 | 100 | 100 | 100 | 100 | ND |
| 82 | 60 | 40 | 65 | 100 | 95 | 85 | 100 | 100 | 100 | ND |
| 83 | 80 | 30 | 60 | 100 | 90 | 80 | 60 | 50 | 60 | ND |

Rate of application of test compound is 1 Kg/Ha. The definitions as shown under Table 4 apply to Table 5.

While the invention has been described in detail and with reference to specific embodiments thereof, it will be apparent to one skilled in the art that various changes and modifications can be made herein without departing from the spirit and scope thereof.

We claim:

1. A compound represented by formula (I):

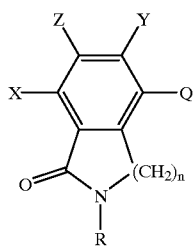

(I)

wherein Q is :

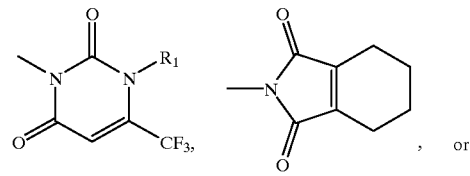

-continued

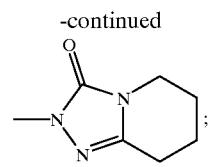

X, Y, and Z are as follows: (i) X is hydrogen, halogen, $(C_1-C_{10})$alkyl, halo$(C_1-C_6)$alkyl, $(C_1-C_6)$alkoxyl, halo$(C_1-C_6)$alkoxyl, cyano, amido, or nitro; Y is hydrogen, halogen, $(C_1-C_6)$alkyl, or halo$(C_1-C_6)$alkyl; and Z is hydrogen, $(C_1-C_3)$alkyl, halogen, amino, nitro, $(C_1-C_3)$ alkoxyl, or hydroxyl with the proviso that when Z is $(C_1-C_3)$alkyl, halogen, amino, nitro, $(C_1-C_3)$alkoxyl, or hydroxyl, X is not a hydrogen and Y is not a hydrogen; or (ii) X and Z are connected to each other to form part of a 4, 5, or 6 membered ring, and Y is as defined above, or Y and Z are connected to each other to form part of a 4, 5, or 6 membered ring and X is defined above;

n is 1 or 2;

R is hydrogen, amino, $(C_1-C_{10})$alkyl, halo$(C_1-C_{10})$alkyl, cyanomethyl, hydroxyl, $(C_1-C_6)$alkoxyl, 2-methoxyethyl, methoxymethyl, cyclopentyl, cyclohexyl, cyclopropylmethyl, prop-2-enyl, prop-2-enyloxy, prop-2-ynyl, ethoxycarbonylmethyl, 2-(methoxycarbonyl)ethyl, phenylmethyl, 4-chlorophenylmethyl, or 4-methoxyphenylmethyl; and $R_1$ is hydrogen, amino, $(C_1-C_6)$alkyl, difluoromethyl, 3-fluoropropyl, methoxymethyl, cyanomethyl, phenylmethyl, prop-2-enyl, prop-2-ynyl, ethoxycarbonylmethyl, or salts thereof.

2. A compound of claim 1, wherein Q is selected from the group consisting of 1-substituted-6-trifluoromethyl-2,4(1H,3H)pyrimidinedion-3-yl, 3,4,5,6-tetrahydrophthalimid-1-yl, and 5,6,7,8-tetrahydro-1,2,4-triazolo[4,3-A]pyridin-3(2H)-on-2-yl.

3. A compound of claim 1, wherein X is chloro; Y is hydrogen or fluoro; and R is $(C_1-C_6)$alkyl, cyclopropylmethyl, halo$(C_1-C_6)$alkyl, prop-2-ynyl, 2-methoxyethyl, or methoxymethyl.

4. A compound of claim 3, wherein Q is 1-substituted-6-trifluoromethyl-2,4(1H,3H)-pyrimidinedion-3-yl; X is chloro; Y is hydrogen or fluoro; n is 1; R is 1-methylethyl; and $R_1$ is methyl or amino.

5. A compound of claim 1, wherein X is hydrogen, halogen, $(C_1-C_6)$alkyl, halo$(C_1-C_3)$alkyl, $(C_1-C_3)$alkoxyl, halo$(C_1-C_3)$alkoxyl, cyano, amido, or nitro; Y is hydrogen, halogen, $(C_1-C_3)$alkyl, or halo$(C_1-C_3)$alkyl; and Z is hydrogen, $(C_1)$alkyl, halogen, amino, nitro, $(C_1)$alkoxyl, or hydroxyl with the proviso that when Z is $(C_1)$alkyl, halogen, amino, nitro, $(C_1)$alkoxyl, or hydroxyl, X is not a hydrogen and Y is not a hydrogen.

6. A herbicidal composition comprising a herbicidally effective amount of at least one compound of claim 1 and a herbicidally compatible carrier therefor.

7. A herbicidal composition comprising a herbicidally effective amount of at least one compound of claim 3 and a herbicidally compatible carrier therefor.

8. A pesticidal composition comprising a herbicidally effective amount of at least one herbicide and a herbicidally compatible carrier therefor, wherein said at least one herbicide is a compound of claim 1.

9. A method of controlling undesired plant growth comprising application of a herbicidally effective amount of a herbicidal composition of claim 6 to a locus where the undesired plants are growing or are expected to grow.

10. A method of controlling undesired plant growth comprising application of a herbicidally effective amount of a herbicidal composition of claim 7 to a locus where the undesired plants are growing or are expected to grow.

* * * * *